United States Patent
Sadeghpour et al.

(10) Patent No.: US 9,937,184 B2
(45) Date of Patent: Apr. 10, 2018

(54) THEOBROMINE COMPOSITIONS USEFUL FOR INCREASING FETAL WEIGHT GAIN AND ENHANCING BONE PROPERTIES

(71) Applicant: THEOCORP HOLDING COMPANY, LLC, Metairie, LA (US)

(72) Inventors: Arman Sadeghpour, Metairie, LA (US); Tetsuo Nakamoto, Kenner, LA (US)

(73) Assignee: THEOCORP HOLDING COMPANY, LLC, Metairie, LA (US)

( * ) Notice: Subject to any disclaimer, the term of this patent is extended or adjusted under 35 U.S.C. 154(b) by 0 days.

(21) Appl. No.: 14/775,104

(22) PCT Filed: Mar. 14, 2014

(86) PCT No.: PCT/US2014/027018
§ 371 (c)(1),
(2) Date: Sep. 11, 2015

(87) PCT Pub. No.: WO2014/152158
PCT Pub. Date: Sep. 25, 2014

(65) Prior Publication Data
US 2016/0030434 A1 Feb. 4, 2016

Related U.S. Application Data

(60) Provisional application No. 61/792,425, filed on Mar. 15, 2013.

(51) Int. Cl.
| | | |
|---|---|---|
| *A61K 31/53* | (2006.01) | |
| *A61K 31/522* | (2006.01) | |
| *C07D 473/08* | (2006.01) | |
| *C12N 5/077* | (2010.01) | |
| *A61K 35/32* | (2015.01) | |
| *C12N 5/0775* | (2010.01) | |
| *A23L 33/105* | (2016.01) | |

(52) U.S. Cl.
CPC .......... *A61K 31/522* (2013.01); *A23L 33/105* (2016.08); *A61K 35/32* (2013.01); *C07D 473/08* (2013.01); *C12N 5/0654* (2013.01); *C12N 5/0663* (2013.01); *A23V 2002/00* (2013.01); *C12N 2500/46* (2013.01); *C12N 2500/76* (2013.01)

(58) Field of Classification Search
CPC ..... A61K 31/53; A61K 31/501; A61K 31/517
See application file for complete search history.

(56) References Cited

U.S. PATENT DOCUMENTS

| | | | |
|---|---|---|---|
| 5,290,558 A | 3/1994 | Leary et al. | |
| 5,663,195 A | 9/1997 | Scolnick | |
| 6,458,375 B1 | 10/2002 | Gertzman et al. | |
| 6,693,104 B2 | 2/2004 | Lee et al. | |
| 2003/0211579 A1* | 11/2003 | Van Ness | C12N 5/0018 435/69.1 |
| 2004/0097612 A1* | 5/2004 | Rosenberg | A61F 2/4644 523/113 |
| 2004/0162289 A1* | 8/2004 | Protter | A61K 31/404 514/241 |
| 2007/0082057 A1* | 4/2007 | Masinaei | A61K 35/32 424/549 |

FOREIGN PATENT DOCUMENTS

WO    2011100671 A2    8/2011

OTHER PUBLICATIONS

International Search Report from corresponding PCT/US2014/027018, dated Jul. 24, 2014.

* cited by examiner

*Primary Examiner* — Ruth A Davis
(74) *Attorney, Agent, or Firm* — McBee Moore Woodward & Vanik IP, LLC; Susan McBee; Chester Moore

(57) ABSTRACT

Compositions and methods for culturing cells with theobromine are provided, as well as cells derived thereby. Theobromine compositions for enhancing bone formation, increasing bone density, increasing interconnections of internal bone, increasing bone mass, treating cartilage and/or bone defects, increasing fetal birth weight, preventing tooth decay, remineralizing a tooth surface, treating dentine hypersensitivity, and application to a bone site to promote new bone growth at the site are also provided.

8 Claims, 11 Drawing Sheets

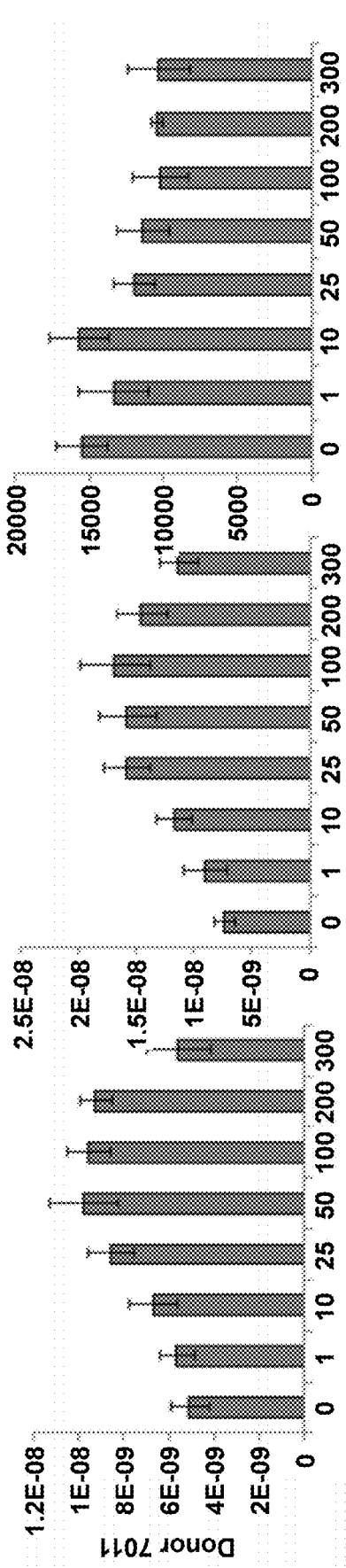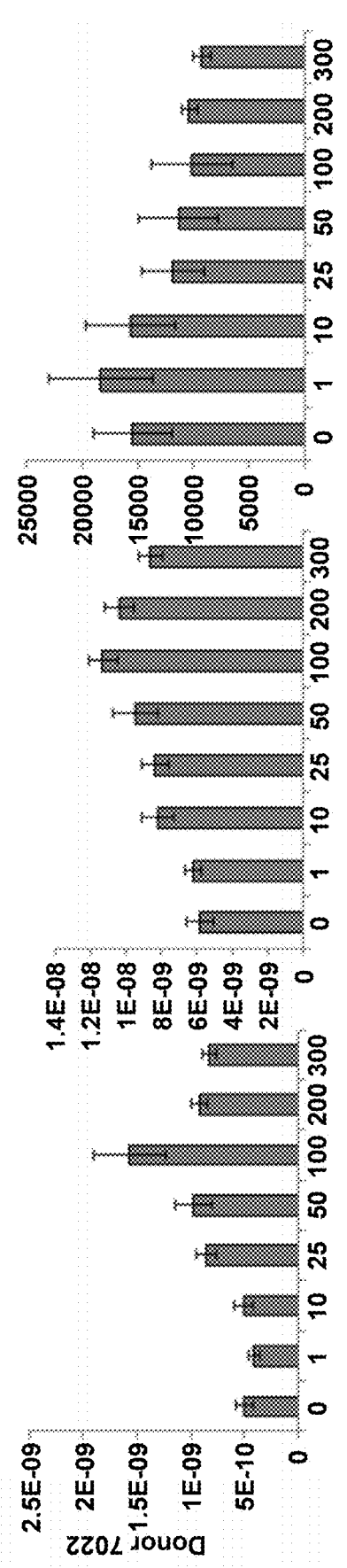
FIG. 1A   FIG. 1B   FIG. 1C

| Cat. | Term | RT | Count | % | P-Value | Benjamini |
|---|---|---|---|---|---|---|
| A | Bone normal 3rd | RT | 21 | 6.7 | 4.6E-14 | 1.9E-10 |
| A | Bone neoplasia 3rd | RT | 15 | 4.8 | 6.8E-9 | 1.4E-5 |
| A | Uncharacterized tissue normal 3rd | RT | 17 | 5.4 | 1.2E-7 | 1.6E-4 |
| A | Eye normal 3rd | RT | 13 | 4.2 | 1.6E-6 | 1.6E-3 |
| A | bone marrow normal 3rd | RT | 11 | 3.5 | 1.7E-6 | 1.4E-3 |
| A | uncharacterized tissue neoplasia 3rd | RT | 7 | 2.2 | 3.7E-6 | 2.5E-3 |
| A | uncharacterized tissue uncharacterized histology $3^{rd}$ | RT | 10 | 3.2 | 7.2E-6 | 4.2E-3 |
| B | Plasma | RT | 17 | 5.4 | 1.0E-5 | 2.0E-3 |
| A | prostate normal $3^{rd}$ | RT | 8 | 2.6 | 1.9E-5 | 9.6E-3 |
| B | Aorta | RT | 11 | 3.5 | 2.4E-5 | 2.3E-3 |
| A | uncharacterized tissue neoplasia $3^{rd}$ | RT | 8 | 2.6 | 3.0E-5 | 1.4E-2 |
| A | placenta normal $3^{rd}$ | RT | 10 | 3.2 | 3.4E-5 | 1.4E-2 |
| B | Liver | RT | 55 | 17.6 | 4.5E-5 | 2.9E-3 |
| A | Cartilage normal $3^{rd}$ | RT | 8 | 2.6 | 4.7E-5 | 1.7E-2 |
| A | Placenta normal $3^{rd}$ | RT | 10 | 3.2 | 7.5E-5 | 2.5E-2 |
| A | uncharacterized tissue neoplasia $3^{rd}$ | RT | 9 | 2.9 | 7.6E-5 | 2.4E-2 |
| A | cartilage uncharacterized histology $3^{rd}$ | RT | 9 | 2.9 | 8.9e-5 | 2.6E-2 |
| A | memory gland normal $3^{rd}$ | RT | 9 | 2.9 | 2.0E-4 | 5.3E-2 |
| A | synovium uncharacterized histology $3^{rd}$ | RT | 11 | 3.5 | 2.1E-4 | 5.2E-2 |
| A | cartilage neoplasia $3^{rd}$ | RT | 9 | 2.9 | 2.7E-4 | 6.4E-2 |
| A | uterus uncharacterized histology $3^{rd}$ | RT | 12 | 3.8 | 3.7E-4 | 8.2E-2 |
| A | vascular normal $3^{rd}$ | RT | 14 | 4.5 | 3.8E-4 | 8.0E-2 |
| A | lung normal $3^{rd}$ | RT | 7 | 2.2 | 4.6E-4 | 9.0E-2 |
| A | placenta normal $3^{rd}$ | RT | 9 | 2.9 | 5.3E-4 | 9.9E-2 |
| A | uncharacterized tissue neoplasia $3^{rd}$ | RT | 8 | 2.6 | 5.6E-4 | 1.0E-1 |
| A | Colon neoplasia $3^{rd}$ | RT | 8 | 2.6 | 6.4E-4 | 1.1E-1 |
| A | cartilage uncharacterized histology $3^{rd}$ | RT | 8 | 2.6 | 7.2E-4 | 1.2E-1 |
| A | Eye normal $3^{rd}$ | RT | 5 | 1.6 | 7.4E-4 | 1.2E-1 |
| A | placenta normal $3^{rd}$ | RT | 6 | 1.9 | 7.7E-4 | 1.2E-1 |
| A | prostate normal $3^{rd}$ | RT | 5 | 1.6 | 8.6E-4 | 1.2E-1 |
| A | uncharacterized tissue neoplasia $3^{rd}$ | RT | 9 | 2.9 | 9.9E-4 | 1.4E-1 |

A – CGAP_EST_QUARTILE
B – UP_TISSUE

FIG. 3

| Cat. | Term | RT | Count | % | P-Value |
|---|---|---|---|---|---|
| B | Plasma | RT | 10 | 9.9 | 1.4E-5 |
| A | Bone normal 3rd | RT | 7 | 6.9 | 3.2E-5 |
| A | Cartilage normal 3rd | RT | 5 | 5.0 | 1.5E-4 |
| A | uncharacterized tissue normal 3rd | RT | 7 | 6.9 | 8.2E-4 |
| A | placenta normal 3rd | RT | 5 | 5.0 | 1.8E-3 |
| A | uncharacterized tissue normal 3rd | RT | 6 | 5.9 | 1.9E-3 |
| A | gastrointestinal tract uncharacterized histology 3rd | RT | 5 | 5.0 | 2.6E-3 |
| A | Eye normal 3rd | RT | 7 | 6.9 | 3.8E-3 |
| A | head and neck neoplasia 3rd | RT | 4 | 4.0 | 6.4E-3 |
| A | uncharacterized tissue neoplasia 3rd | RT | 3 | 3.0 | 6.5E-3 |
| A | Uncharacterized tissue uncharacterized histology 3rd | RT | 4 | 4.0 | 7.4E-3 |
| A | Prostate normal 3rd | RT | 3 | 3.0 | 7.4E-3 |
| B | Cartilage | RT | 3 | 3.0 | 7.6E-3 |
| A | Thymus uncharacterized histology 3rd | RT | 4 | 4.0 | 7.7E-3 |
| A | uncharacterized tissue uncharacterized histology 3rd | RT | 4 | 4.0 | 7.9E-3 |
| B | Prostate | RT | 9 | 8.9 | 8.1E-3 |
| A | Uncharacterized tissue uncharacterized histology 3rd | RT | 4 | 4.0 | 8.4E-3 |
| A | placenta normal 3rd | RT | 3 | 3.0 | 9.0E-3 |
| A | uncharacterized tissue uncharacterized histology 3rd | RT | 4 | 4.0 | 9.3E-3 |
| A | stomach normal 3rd | RT | 3 | 3.0 | 1.2E-2 |
| A | placenta normal 3rd | RT | 4 | 4.0 | 1.3E-2 |
| A | Bone neoplasia 3rd | RT | 4 | 4.0 | 1.6E-2 |
| A | placenta normal 3rd | RT | 5 | 5.0 | 1.8E-2 |
| B | Blood | RT | 9 | 8.9 | 1.9E-2 |
| A | colon neoplasia 3rd | RT | 4 | 4.0 | 2.1E-2 |
| A | Colon normal | RT | 3 | 3.0 | 2.3E-2 |
| A | cerebrum normal 3rd | RT | 3 | 3.0 | 2.3E-2 |
| A | prostate normal 3rd | RT | 3 | 3.0 | 2.3E-2 |
| A | thyroid neoplasia 3rd | RT | 3 | 3.0 | 2.3E-2 |
| A | synovium uncharacterized histology 3rd | RT | 4 | 4.0 | 2.5E-2 |
| A | cartilage normal 3rd | RT | 5 | 5.0 | 2.6E-2 |

A – CGAP_EST_QUARTILE
B – UP_TISSUE

FIG. 4

| Cat. | Term | RT | Count | % | P-Value | Benjamini |
|---|---|---|---|---|---|---|
| B | Epithelium | RT | 151 | 29.2 | 1.6E-23 | 3.4E-21 |
| A | thyroid neoplasia 3rd | RT | 19 | 3.7 | 3.4E-10 | 1.8E-6 |
| A | uterus neoplasia 3rd | RT | 17 | 3.3 | 1.5E-9 | 4.1E-6 |
| A | uncharacterized tissue neoplasia 3rd | RT | 19 | 3.7 | 4.8E-9 | 8.4E-6 |
| A | Lymph node normal 3rd | RT | 21 | 4.1 | 5.6E-8 | 7.4E-5 |
| B | Brain | RT | 260 | 50.2 | 6.0E-8 | 6.6E-6 |
| A | uterus uncharacterized histology 3rd | RT | 13 | 2.5 | 8.5E-8 | 9.0E-5 |
| A | Nervous normal 3rd | RT | 26 | 5.0 | 1.0E-7 | 8.9E-5 |
| A | Soft tissue normal 3rd | RT | 20 | 3.9 | 1.5E-7 | 1.1E-4 |
| A | Uncharacterized tissue uncharacterized histology 3rd | RT | 22 | 4.2 | 1.5E-7 | 1.0E-4 |
| A | Placenta normal 3rd | RT | 16 | 3.1 | 2.8E-7 | 1.6E-4 |
| A | placenta normal 3rd | RT | 15 | 2.9 | 4.1E-7 | 2.2E-4 |
| A | Thyroid neoplasia 3rd | RT | 16 | 3.1 | 4.2E-7 | 2.0E-4 |
| A | Mammary gland normal 3rd | RT | 17 | 3.3 | 4.4E-7 | 2.0E-4 |
| A | Head and neck neoplasia 3rd | RT | 17 | 3.3 | 4.9E-7 | 2.0E-4 |
| A | bone normal 3rd | RT | 21 | 4.1 | 6.2E-7 | 2.3E-4 |
| A | placenta normal 3rd | RT | 14 | 2.7 | 7.3E-7 | 2.6E-4 |
| A | thymus normal 3rd | RT | 18 | 3.5 | 9.4E-7 | 3.1E-4 |
| A | placenta normal 3rd | RT | 13 | 2.5 | 1.0E-6 | 3.2E-4 |
| A | Brain neoplasia 3rd | RT | 24 | 4.6 | 1.1E-6 | 3.3E-4 |
| A | uterus uncharacterized histology 3rd | RT | 16 | 3.1 | 1.4E-6 | 3.8E-4 |
| A | Testis normal 3rd | RT | 13 | 2.5 | 1.5E-6 | 3.9E-4 |
| A | lymph node normal 3rd | RT | 19 | 3.7 | 1.6E-6 | 4.2E-4 |
| A | brain neoplasia 3rd | RT | 13 | 2.5 | 1.9E-6 | 4.5E-4 |
| A | Placenta normal 3rd | RT | 8 | 1.5 | 2.7E-6 | 6.1E-4 |
| A | Mammary gland neoplasia 3rd | RT | 11 | 2.1 | 3.3E-6 | 7.3E-4 |
| A | Colon neoplasia 3rd | RT | 15 | 2.9 | 4.9E-6 | 1.0E-3 |
| A | Prostate normal 3rd | RT | 15 | 2.9 | 4.9E-6 | 1.0E-3 |
| A | Testis normal 3rd | RT | 10 | 1.9 | 7.1E-6 | 1.4E-3 |
| A | placenta normal 3rd | RT | 10 | 1.9 | 7.1E-6 | 1.4E-3 |
| A | stomach normal 3rd | RT | 9 | 1.7 | 7.4E-6 | 1.5E-3 |

A – CGAP_EST_QUARTILE
B – UP_TISSUE

FIG. 5

| Donor | Term | RT | Count | % | P-Value | Benjamini |
|---|---|---|---|---|---|---|
| 281 | ECM receptor interaction | RT | 13 | 4.2 | 1.8E-8 | 1.8E-6 |
| | vascular smooth muscle contraction | RT | 10 | 3.2 | 1.4E-4 | 7.1E-3 |
| | focal adhesion | RT | 13 | 4.2 | 1.9E-4 | 6.4E-3 |
| 7023 | ECM receptor interaction | RT | 5 | 5.0 | 9.1E-4 | 3.3E-2 |
| | focal adhesion | RT | 5 | 5.0 | 2.0E-2 | 3.2E-1 |
| 7057 | axon guidance | RT | 11 | 2.1 | 1.2E-3 | 1.2E-1 |
| | endometrial cancer | RT | 7 | 1.4 | 1.6E-3 | 8.4E-2 |
| | focal adhesion | RT | 13 | 2.5 | 3.6E-3 | 1.3E-1 |

FIG. 6

THEOBROMINE COMPOSITIONS USEFUL FOR INCREASING FETAL WEIGHT GAIN AND ENHANCING BONE PROPERTIES

CROSS REFERENCE TO RELATED APPLICATIONS

This application is a § 371 National Stage Application of PCT/US2014/027018, filed 14 Mar. 2014, which claims priority to U.S. 61/792,425, filed 15 Mar. 2013.

BACKGROUND

1. Field

The present disclosure relates to compositions and methods for enhancing bone formation, increasing bone density, increasing interconnections of internal bone, increasing bone mass, treating cartilage and/or bone defects, or combinations thereof, in a subject in need thereof, improving maternal and/or child health during the stages of preconception, pregnancy, lactation, and/or postpartum, and increasing osteoblastic/osteogenic activity in mesenchymal stem cells (MSCs; also called "marrow stromal cells" or "multipotent stromal cells"). More particularly, said compositions comprise cocoa extract.

2. Description of Related Art

Theobromine (IUPAC name: 3,7-dimethyl-2,3,6,7-tetrahydro-1H-purine-2,6-dione; also known as 3,7-dimethylxanthine) is a white (or colorless) bitter-tasting crystalline powder with a sublimation point of 290-295° C., a melting point of 357° C., and a molecular weight of 180.16 g/mol. The solubility of theobromine in water is 1.0 g/2 L; in boiling water, it is 1.0 g/150 mL, and in 95% ethanol it is 1.0 g/2.2 L. Theobromine is related chemically to caffeine and theophylline, and is found in numerous foods including chocolate, cocoa, tea leaves, and acai berries. The chemical structures of theobromine, theophylline (1,3-dimethylxanthine), and caffeine (1,3,7-trimethylxanthine) are given below as formulae I, II, and III, respectively.

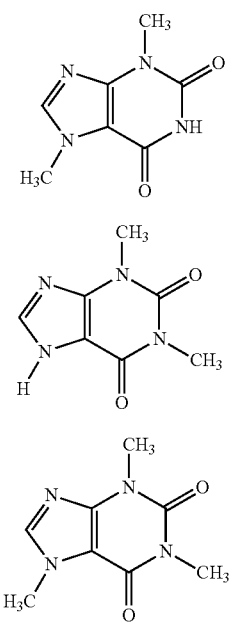

Theobromine is found naturally in cacao beans (*Theobroma cacao*) at a concentration of from about 1.5% to about 3%, and in the husk of the bean at a concentration of from about 0.7% to about 1.2%, or about 15 to about 30 g/Kg (Winholdz, 1983). Though part of the same chemical family, one must distinguish the stimulant effects of theobromine from those of caffeine. Caffeine acts relatively quickly, and its main effect on humans is increased mental alertness; theobromine's effect is subtler, and causes a mood elevation that is milder longer-lasting than that of caffeine. Theobromine's plasma half-life ($t_{1/2}$) in the bloodstream is six hours, while caffeine's is only two hours. Another difference is that theobromine is not physiologically addictive, producing no withdrawal symptoms after prolonged regular consumption, while caffeine has been proven to be physiologically addictive and linked with many cases of proven withdrawal.

As used herein, "theobromine" refers to theobromine, a salt or double salt of theobromine, or a co-crystal comprising theobromine.

Two independent studies conducted in the 1980's found that the average level of theobromine in eight varieties of commercial cocoa powder was 1.89% (Shively & Tarka, 1984 and Zoumas et al., 1980). Of particular relevance are the normal levels of theobromine found in commercially-available foodstuffs, shown below in TABLE 1.

TABLE 1

| Food Type | Theobromine Content |
| --- | --- |
| hot chocolate beverages | 65 mg/5-oz serving |
| chocolate milk (from instant or sweetened cocoa powder) | 58 mg/serving |
| hot cocoa (average of 9 commercial mixes) | 62 mg/serving |
| cocoa cereals* | 0.695 mg/g |
| chocolate bakery products* | 1.47 mg/g |
| chocolate toppings* | 1.95 mg/g |
| cocoa beverages* | 2.66 mg/g |
| chocolate ice cream* | 0.621 mg/g |
| chocolate milk* | 0.226 mg/g |
| chocolate pudding* | 74.8 mg/serving |
| carob products* | 0-0.504 mg/g |

Sources: Zoumas, et al., 1980; Blauch & Tarka, 1983; Shivley & Tarka, 1984; Craig & Nguyen, 1984.
*Theobromine content determined by HPLC/reverse-phase column chromatography Dark chocolate contains the highest levels of theobromine per serving of any type of chocolate, but the concentrations tends to vary between about 0.36% and about 0.63%. To put this into perspective with the foodstuffs mentioned in TABLE 1, a one-ounce bar of dark chocolate contains about 130 mg of theobromine, while a one ounce bar of milk chocolate contains about 44 mg of theobromine. Thus, the concentration of theobromine in a one-ounce bar of dark chocolate is approximately two times the amount in a 5-ounce cup of hot chocolate. For a 143-pound human being to achieve a toxic level of theobromine in their blood, they would have to ingest approximately 86 one-ounce milk chocolate bars in one sitting.

Theobromine can also be isolated or produced as an amine salt (e.g., the ethylene diamine salt thereof) or a double salt thereof (e.g., with alkali metal salts or alkaline earth metal salts of organic acids, for example alkali or alkaline earth metal salts of acetic, gluconic, benzoic, or salicylic acid).

The double salts may be prepared either to make the theobromine more water soluble, or to make insoluble complexes.

In 1966, Strålfors reported a reduction of dental caries in hamsters that were fed diets rich in chocolate. The Strålfors study examined the effect on hamster caries by comparing cocoa powder, defatted cocoa powder, and cocoa fat. Pure cocoa powder inhibited dental caries by 84%, 75%, 60%, and 42% when the cocoa powder comprised 20%, 10%, 5%, and 2% percent of the hamster diet, respectively. Defatted cocoa showed a significantly higher anti-caries effect than did fat-containing cocoa powder, but cocoa butter alone (comprising 15% of the hamster's diet) increased dental caries significantly (Strålfors A. "Effect on Hamster Caries by Dialyzed, Detanned or Carbon-treated Water-Extract of Cocoa" Arch Oral Biol. 1966; 11:609-15.

In a follow up study, Strålfors studied the nonfat portions of the cocoa powder and demonstrated that cocoa powder washed with water possessed considerably less anti-cariogenic effect than unwashed cocoa powder. Nevertheless, Strålfors still observed a considerable anti-caries effect in the washed cocoa powder group, "indicating an existence of a non-water soluble cariostatic factor," and alluded to the existence of "two caries-inhibitory substances in cocoa: one water-soluble, and another which is sparingly soluble in water" (Strålfors, A., 1966).

Subsequent studies suggested that apatite crystals grown in vitro in the presence of theobromine were significantly larger than those grown in the absence of theobromine (see, e.g., U.S. Pat. Nos. 5,919,426 and 6,183,711, each of which is incorporated by reference in its entirety). Ingestion of theobromine by lactating rats was correlated with increased hydroxylapatite crystallite size (higher crystallinity) in the whole first molars of nursing pups exposed to theobromine, versus controls, as well as increased resistance to acid dissolution (see id.). The femurs of nursing female pups exposed to theobromine demonstrated higher crystallinity, and were stronger and stiffer than gender-matched controls; the femurs of male pups, however, did not show this relationship (see id.).

The Hall-Petch relationship, however, dictates that the resistance of a solid material to permanent deformation (e.g., its indentation hardness) increases as the particle size decreases. Consequently, the increased hydroxylapatite crystallinity observed after exposure to theobromine—coupled with the Hall-Petch relationship—suggests that the resistance of bone and teeth to indentation and permanent deformation should decrease after exposure to theobromine due to the larger crystal size. This suggestion finds support in recent work, demonstrating that "the hardness of [hydroxylapatite] follows the Hall-Petch relationship as the grain size decreases from sub-micrometers to nanometers" (Wang J. et al "Nanocrystalline hydroxyapatite with simultaneous enhancements in hardness and toughness" Biomaterials. 2009; 30:6565-72). Another study suggests that the "hardness" of hydroxylapatite has little to do with particle size, showing almost no change in hardness with decreasing grain size, yet demonstrates that the "fracture toughness" of hydroxylapatite is increased with decreasing particle size (Mazaheri M, et al "Effect of a novel sintering process on mechanical properties of hydroxyapatite ceramics." J. Alloys Compd. 2009; 471:180-4). A study of human adult and primary (baby) teeth demonstrated that, "[w]hen compared to the adult tooth, the baby enamel was thinner, softer, more prone to fracture, and possessed larger [hydroxylapatite] grains" (Low I M, et al. "Mapping the structure, composition and mechanical properties of human teeth." Mater Sci Eng C Mater Biol App. 2008; 28:243-47.).

Because of such conflicting and paradoxical results, one cannot extrapolate the known characteristics and responses of hydroxylapatite to environmental factors to predict a reliable or accurate result cannot be predicted simply by evaluating the prior art and extrapolating a result.

MSCs are characterized by their ability to produce daughter stem cells, and to differentiate into many distinct cell types including, but not limited to, osteoblasts, stromal cells that support hematopoiesis and osteoclastogenesis, chondrocytes, myocytes, adipocytes of the bone marrow, neuronal cells, and $\beta$-pancreatic islet cells. Consequently, MSCs provide osteoblasts and stromal cells needed for bone development, bone remodeling and hematopoiesis throughout life.

In humans, bone formation begins during the first 6-8 weeks of fetal development. Progenitor stem cells of mesenchymal origin migrate to predetermined sites, where they either: (a) condense, proliferate, and differentiate into bone-forming cells (osteoblasts), a process observed in the skull and referred to as "intramembranous bone formation;" or, (b) condense, proliferate and differentiate into cartilage-forming cells (chondroblasts) as intermediates, which are subsequently replaced with bone-forming cells. More specifically, mesenchymal stem cells differentiate into chondrocytes. The chondrocytes then become calcified, undergo hypertrophy and are replaced by newly formed bone made by differentiated osteoblasts, which now are present at the site. Subsequently, the mineralized bone is extensively remodeled, thereafter becoming occupied by an ossicle filled with functional bone-marrow elements. This process is observed in long bones and referred to as "endochondral bone formation." In postfetal life, bone has the capacity to repair itself upon injury by mimicking the cellular process of embryonic endochondral bone development. That is, mesenchymal progenitor stem cells from the bone-marrow, periosteum, and muscle can be induced to migrate to the defect site and begin the cascade of events described above. There, they accumulate, proliferate, and differentiate into cartilage, which is subsequently replaced with newly formed bone.

MSCs are extremely rare in the bone marrow, and earlier attempts to expand them ex vivo from rodent or human marrow have proven difficult. Moreover, inducing proliferation and differentiation of progenitor cells into functional bone, cartilage, tendon, and/or ligamentous tissue has been shown to require various proteins, including, but not limited to, members of the family of bone morphogenetic proteins (BMPs) and members of the TGF-$\beta$ superfamily of growth factors. Manufacture, isolation, and purification of such proteins is necessarily more complex and expensive than that of small-molecule chemical compounds because proteins are larger, more complex, and are synthesized by a living cell.

Thus, there remains a need for small-molecule chemical compounds—especially ones known to be non-toxic—capable of inducing proliferation of progenitor cells into functional bone, cartilage, tendon, and/or ligamentous tissue.

The solution to this technical problem is provided by the embodiments characterized in the claims.

BRIEF SUMMARY

The present disclosure provides, in one embodiment, an isolated cell in a culture medium, said culture medium comprising theobromine, a salt or double salt of theobromine, or a co-crystal comprising theobromine. In a further embodiment, the isolated cell is a mammalian cell. In a further embodiment, the isolated cell is a stem cell. In a further embodiment, the stem cell is a mesenchymal stem cell. In a further embodiment, the theobromine, salt or double salt of theobromine, or co-crystal comprising theobromine is present in an amount from 1 to 300 µM.

The present disclosure provides, in another embodiment, a method of culturing a cell, the method comprising: a) culturing said cell in a culture medium, wherein said culture medium comprises theobromine, a salt or double salt of theobromine, or a co-crystal comprising theobromine. In a further embodiment, the cell is a mammalian cell. In a further embodiment, the cell is a stem cell. In a further embodiment, the stem cell is a mesenchymal stem cell. In a further embodiment, the theobromine is from 1 to 300 µM.

The present disclosure provides, in another embodiment, a culture medium comprising theobromine, a salt or double salt of theobromine, or a co-crystal comprising theobromine. In a further embodiment, the theobromine, salt or double salt of theobromine, or co-crystal comprising theobromine is present in an amount from 1 to 300 µM. In a further embodiment, the theobromine, salt or double salt of theobromine, or co-crystal comprising theobromine is from 1 to 100 µM.

The present disclosure provides, in another embodiment, use of a composition comprising theobromine, a salt or double salt of theobromine, or a co-crystal comprising theobromine, a salt or double salt of theobromine, or a co-crystal comprising theobromine for enhancing bone formation, increasing bone density, increasing interconnections of internal bone, increasing bone mass, treating cartilage and/or bone defects, increasing fetal birth weight, or combinations thereof, in a subject in need thereof.

The present disclosure provides, in another embodiment, use of a composition comprising theobromine, a salt or double salt of theobromine, or a co-crystal comprising theobromine, a salt or double salt of theobromine, or a co-crystal comprising theobromine for preventing tooth decay, remineralizing a tooth surface, treating dentine hypersensitivity, or combinations thereof, in a subject in need thereof.

The present disclosure provides, in another embodiment, a method for improving maternal and/or child health during the stages of preconception, pregnancy, lactation, and/or postpartum comprising: administering a composition a) to a mother during pregnancy and/or lactation; or b) to a child during the stage of postpartum; wherein the composition comprises theobromine, a salt or double salt of theobromine, or a co-crystal comprising theobromine. In a further embodiment, the composition benefits at least one of the mother and child, wherein said benefit is selected from the group consisting of increased fetal weight gain, enhanced bone formation, increased bone density, increased interconnections of internal bone, increased bone mass, and combinations thereof.

The present disclosure provides, in another embodiment, a composition comprising: a) demineralized osteogenic bone powder with a particle size of about 250 µm to about 5 mm; and b) theobromine, a salt or double salt of theobromine, or a co-crystal comprising theobromine.

In a further embodiment, the present disclosure provides use of a composition comprising: a) demineralized osteogenic bone powder with a particle size of about 250 µm to about 5 mm; and b) theobromine, a salt or double salt of theobromine, or a co-crystal comprising theobromine.

In a further embodiment, the present disclosure provides use of a composition comprising a bone cement and theobromine. For example, without intending to be limited, the bone cement may be formed by combining calcium and phosphate precursors in an aqueous solution, which initially forms a paste but then hardens into a hydroxyapatite bone cement when used. The bone cement may be a composition comprising at least one calcium phosphate, at least one sodium phosphate, and theobromine, a salt or double salt of theobromine, or a co-crystal comprising theobromine.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

FIG. 1 shows dose-dependent upregulation of early osteogenic markers by theobromine. Human MSCs from two different donors (7011 & 7022) were subjected to 8 days of culture in the presence of osteogenic supplements and the indicated doses of theobromine (1 to 300 µM). After 8 days, monolayers were assayed for ALP activity (FIG. 1A; arbitrary rate units/cell), OPG secretion (FIG. 1B; µg/cell/48 h), and cell number (FIG. 1C; cells recovered/cm$^2$).

FIG. 3 shows tissue clustering for hMSC donor 281 (p-value<0.001); entries 1-31 of 31 total.

FIG. 4 shows tissue clustering for hMSC donor 7023 (p-value<0.001); entries 1-31 of 104 total.

FIG. 5 shows tissue clustering for hMSC donor 7057 (p-value<0.001); entries 1-31 of 175 total.

FIG. 6 shows pathway clustering for donors 281, 7023, and 7057; note that focal adhesion and ECM interactions are present for 2 of the 3 donors.

DETAILED DESCRIPTION

Figure 2A:
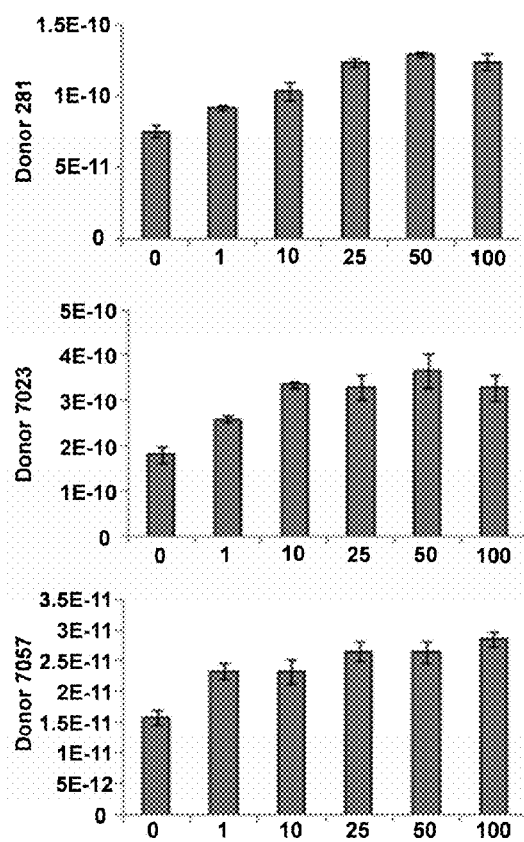
FIG. 2 shows increased ALP activity upon treatment with 10-100 µM Thb for 8 days. Human MSCs from three different donors (281, 7023 & 7057) were subjected to 8 days of culture in the presence of osteogenic supplements and the indicated doses of theobromine (1 to 100 µM). After 8 days, monolayers were assayed for ALP activity (FIG. 2A; arbitrary rate units/cell) and cell number (FIG. 2B; cells recovered/cm$^2$).

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

As shown by the data below, the expression of genes implicated in osteogenesis is significantly increased in MSCs after incubation with theobromine. Also shown below, theobromine is involved in promoting fetal weight gain, enhancing bone formation, increasing bone density, increasing interconnections of internal bone, increasing bone mass, treating cartilage and/or bone defects, or combinations thereof, in a subject in need thereof, and improving maternal and/or child health during the stages of preconception, pregnancy, lactation, and/or postpartum. Without wishing to be bound by theory, Applicant believes these results may occur through the actions of theobromine on MSCs.

Adults with higher birth weights are less likely to suffer or die from cardiovascular disease and suffer from high blood pressure. Therefore, reduced adult cardiovascular-related death and decreased systolic blood pressure are possible outcomes of adequate theobromine supply during preconception and pregnancy. One embodiment of the present disclosure provides for overall improvement of pregnancy outcomes and/or birth weight related to theobromine supplementation, resulting in increased fetal weight gain, enhanced bone formation, increased bone density, increased interconnections of internal bone, increased bone mass, and combinations thereof.

In accordance with another embodiment of the present invention, maternal nutritional formulations (including nutritional supplements and foods) comprising theobromine are provided for preconception, pregnancy, and lactation/postpartum. The maternal route of supplementation represents an opportunity to supply theobromine to the developing infant in an effective and efficient manner in addition to or instead of infant formula formulated with theobromine.

In accordance with another embodiment of the present invention, infant nutritional formulations (including nutritional supplements and foods) comprising theobromine are provided.

Preconception is defined as the period during which a women is attempting to become pregnant. This is important because preparing for pregnancy is just as important as being pregnant and many women who are trying to become pregnant are pregnant for a month or more before they realize it. Lactation/postpartum is from delivery until two years later, or until breast-feeding is stopped. It will be understood that supplementation can have benefits for the mother even if the mother is not breast-feeding the child. It will be understood that supplementation is preferred, but not required, during each stage, and is preferred, but not required, continuously throughout each stage.

Nor are the supplements described herein limited to maternal and/or infant use. Any human in need thereof (e.g., man, woman, child of either gender) in need of enhancing bone formation, increasing bone density, increasing interconnections of internal bone, increasing bone mass, treating cartilage and/or bone defects, or combinations thereof, may benefit from the supplements described herein. For example, and without limitation, a person in need thereof could be one at risk of developing or diagnosed with osteoporosis.

Osteoporosis is a disease of bone that leads to an increased risk of fracture. In a person suffering from osteoporosis, bone mineral density is reduced, bone microarchitecture is disrupted, and the amount and variety of non-collagenous proteins in bone is altered. The World Health Organization (WHO) defines osteoporosis (in women) as a bone mineral density 2.5 standard deviations below peak bone mass (versus an average 30-year-old healthy female). Osteoporosis is most common in women after menopause, where it is called postmenopausal osteoporosis, but may also develop in men, and may occur in anyone in the presence of particular hormonal disorders and other chronic diseases or as a result of medications (e.g., glucocorticoids) where the disease is called steroid- or glucocorticoid-induced osteoporosis, and as a result of nutritional deficiency states or other metabolic disorders, including, but not limited to, hyponatremia or as a secondary consequence of cancer. Given its influence on the risk of fragility fracture, osteoporosis may significantly affect life expectancy and quality of life. About 20 percent of senior citizens who suffer a hip fracture die within a year of fracture. About 20 percent of individuals with a hip fracture end up in a nursing home within a year. Hip fractures account for 300,000 hospitalizations each year. The direct care costs for osteoporotic fractures alone are already up to $18 billion each year. That number is expected to increase if action to prevent osteoporosis is not taken now. With healthy nutrition, physical activity every day, and regular medical check-ups and screenings, people of all ages can have strong bones and live longer, healthier lives. Therefore, reduced incidence of osteoporosis is a possible outcome of adequate theobromine supply to a person in need thereof. One embodiment of the present disclosure provides compositions and methods for treating osteoporosis, said compositions comprising theobromine.

Any biologically acceptable dosage forms, and combinations thereof, are contemplated by the inventive subject matter. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables, infusions, health bars, confections, cereals, cereal coatings, foods, nutritive foods, functional foods, dental varnish, and combinations thereof. For example, a theobromine varnish (a concentrated form of theobromine for application to the surface, the enamel, the dentine, and or cementum of at least one tooth) may provide topical theobromine therapy to a person in need thereof to, for example and without limitation, help prevent decay, remineralize the tooth surface, and treat dentine hypersensitivity. The preparations of the above dosage forms are well known to persons of ordinary skill in the art.

Preferably, foods enriched with theobromine are selected from the group including:
baked goods and mixes (e.g., bread); chewing gum; breakfast cereals; cheese products; nuts and nut products; gelatins, pudding, custard, and fillings; frozen dairy products; milk products (e.g., meal-replacement beverages, yogurt, yogurt drinks); dairy product analogs; hard candy; soft candy; soups and soup mixes; snack foods; beverages; processed fruit juice; fruit smoothies; powdered fruit-flavored drinks; processed vegetable juice; sports or isotonic drinks; meal-replacement beverages;

non-milk-based beverages (e.g., soy milk); bottled water (e.g., vitamin, enhanced, and bottled waters); coffee; tea; fats and oils; fish products; plant protein products; poultry products; and meat products;

more preferably, baked goods and mixes; breakfast cereals; gelatins, puddings, and fillings; dairy product analogs; soups and soup mixes; poultry products; nuts and nut products; frozen dairy; milk products; soft candy; plant protein products; fats and oils;

more preferably, nuts and nut products; frozen dairy; milk products; soft candy; plant protein products; fats and oils; and more preferably nuts and nut-based products; milk products; soft candy. A further summary is provided in TABLE 2.

TABLE 2

Summary of Individual Proposed Food-Uses and Use-Levels for Theobromine

| Food Category | Proposed Food Use | Theobromine (mg/serving) | Serving Size (g or mL) | Use Level (%) |
|---|---|---|---|---|
| Baked Goods & Baking Mixes | Bread | 15 | 25 | 0.060 |
| Breakfast Cereals | Instant or Regular Oatmeal | 30 | 37 | 0.13 |
|  | Ready-to-Eat Cereals | 30 | 30 | 0.10 |
| Beverages & Beverage Bases | Sports & Isotonic Drinks | 60 | 488 | 0.012 |
|  | Meal-Replacement Beverages, Non Milk-Based | 75 | 240 | 0.017 |
| Chewing Gum | Chewing Gum | 10 | 3 | 0.33 |
| Coffee/Tea | Tea | 40 | 488 | 0.0082 |
| Dairy Product Analogs | Soy Mil | 40 | 250 | 0.016 |
| Gelatins, Puddings, & Custard | Gelatin | 40 | 85 | 0.047 |
| Hard Candy | Mints | 5 | 2 | 0.25 |
| Milk Products | Meal-Replacement Beverages, Milk-Based | 75 | 240 | 0.031 |
|  | Yogurt (fresh, not chocolate) | 50 | 170 | 0.029 |
|  | Yogurt Drinks | 25 | 28 | 0.089 |
| Processed Fruits & Fruit Juices | Fruit Smoothies | 50 | 366 | 0.014 |
|  | Powdered Fruit-Flavored Drinks | 50 | 8 | 0.62 |

The supplement is preferably administered during one or more of the three stages of pregnancy: preconception, pregnancy, and during lactation/postpartum. Preferably, the supplement is administered during preconception, pregnancy, and during lactation/postpartum. Preferably, the maternal supplement is administered during preconception and during pregnancy and during lactation/postpartum. Preferably, the maternal supplement is administered during lactation/postpartum.

In accordance with another embodiment of the present invention, a surgical bone defect filling product comprising theobromine is provided. More specifically, the surgical bone defect filling product comprises theobromine and allograft bone. The surgical bone defect filling product may further comprise gelatin, with the gelatin being cross linked by lyophilization of the composition to form a solid composition which is later rehydrated for application to a bone defect area. The surgical bone defect filling product may be a shaped osteoimplant, meaning a predetermined or regular form or configuration in contrast to an indeterminate or vague form or configuration and by way of example would be characteristic to a wedge, cylinder, disk, plate sheet, tube and the like. The surgical bone defect filling product may comprise partially demineralized bone material (e.g., having a residual calcium content ranging between about 3 to about 10%, preferably 4 to 6%). Methods of manufacturing suitable demineralized bone material are known to those of ordinary skill in the art and discussed, for example, in WO 2007/133722, which is incorporated by reference herein.

In accordance with another embodiment of the present invention, a sterile malleable bone composition for application to a bone defect site to promote new bone growth at the site comprising theobromine and demineralized osteogenic bone powder with a particle size ranging from about 250 to about 750 microns is provided. In another embodiment, the composition comprises theobromine and demineralized osteogenic bone particles with a particle size ranging from about 0.1 to about 5 mm, from about 0.1 to about 4 mm, from about 0.1 to about 3 mm, from about 0.1 to about 2 mm, and from about 0.1 to about 1 mm.

Example 1: Fetal Calvaria Cells

Fetal calvaria cells were cultured in 24-well culture plates using D-MEM and supplemented with 10% (V/V) FBS, 100 U/mL penicillin, and 100 μg/mL streptomycin. The cells were cultured in medium with various concentrations (0.1, 1.0, 10, 20, 40, 60, and 100 μM) of theobromine and without theobromine (control) for 96 hours, then counted using trypan blue dye exclusion method after culture. The results are shown below in TABLE 3.

TABLE 3

| Theobromine (μM) | Cells/well (×10$^3$) | % vs. control |
|---|---|---|
| 0 | 72.58 | 100 |
| 0.1 | 56.53 | 78 |
| 1.0 | 82.96 | 114 |
| 10 | 75.64 | 104 |

TABLE 3-continued

| Theobromine ($\mu$M) | Cells/well ($\times 10^3$) | % vs. control |
|---|---|---|
| 20 | 82.18 | 113 |
| 40 | 63.96 | 88 |
| 60 | 56.04 | 77 |
| 100 | 43.42 | 60 |

The data of TABLE 3 demonstrate a slight increase in cell proliferation at theobromine concentrations between 1.0 and 20 $\mu$M.

Example 2: Osteoblast-Like Cells (UMR 106-01)

UMR 106-01 rat obsteoblast-like cells were cultured in 24-well culture plates using D-MEM supplemented with 10% (V/V) FBS, 100 U/mL penicillin, and 100 $\mu$g/mL streptomycin. The cells were cultured in medium with various concentrations (0.0027, 0.027, 0.27, 2.7, 27, and 270 $\mu$M) of theobromine and without theobromine (control) for 96 hours, then counted using trypan blue dye exclusion method. The results are shown in TABLE 4. Statistical analysis was done using Student's t-test. P-values less than 5% were considered statistically significant.

TABLE 4

| Theobromine ($\mu$M) | Cell Number/mL Mean ± SEM ($\times 10^4$) | % change | p-value |
|---|---|---|---|
| 0 | 101.50 ± 2.84 | 0 | — |
| 0.0027 | 112.50 ± 7.38 | 14 | 0.19 |
| 0.027 | 129.00 ± 6.05 | 27 | 0.002 |
| 0.27 | 126.50 ± 5.04 | 26 | 0.002 |
| 2.7 | 121.00 3.35 | 20 | 0.001 |
| 27 | 120.50 ± 7.07 | 20 | 0.008 |
| 270 | 134.50 ± 7.88 | 33 | 0.003 |

The data of TABLE 4 demonstrate a significant increase in proliferation of osteoblast-like cells at theobromine concentrations between 0.027 and 270 $\mu$M. These results stand in contrast with prior art results demonstrating that caffeine (1,3,7-trimethylxanthine, with one more methyl group—at the 1 position—than theobromine) inhibits cell proliferation (Kamagata-Kiyoura, Y., Ohta, M., Cheuk, G., Yazdani, M., Saltzman, M. J. and Nakamoto, T. Combined effects of caffeine and prostaglandin E2 on the proliferation of osteoblast-like cells (UMR 106-01). *J. Periodontal.* 1999; 70:283-288).

Example 3: Rodent Protocol

Animals: Ten pregnant Sprague Dawley rats were ordered from Harlan Laboratories and shipped as soon as pregnancy was confirmed (day 1).

Prenatal: Beginning on day 7, a specially prepared diet comprising theobromine (Thb) powder was fed to the experimental group (5 female rats) and control group without Thb (5 female rats). The Thb dose was approximately 1 mg per 100 g body mass in food. To prevent the need for constant weighing of pregnant and nursing animals, the average weight during pregnancy and the average food intake was approximated. Approximations were based on the study sponsor's prior experience, data from Harlan laboratories, and data from Keenan et al "The Effects of Overfeeding and Dietary Restriction on Sprague-Dawley Rat Survival and Early Pathology Biomarkers of Aging" *Toxicol Pathol.* 1994; 22:300. To attain approximately 1 mg of Thb per 100 g body mass, the test diet consisted of 113 mg of finely ground Thb powder mixed well with 1 kg of powdered chow. Birth was predicted to occur during the afternoon of day 22 or early morning of day 23. Postnatal theobromine doses were as follows: 88 mg/kg for postnatal days 1 to 14; 59 mg/kg for postnatal days 14 to 22. After weaning, theobromine was added to the diet of offspring as follows: 89 mg/kg for postnatal days 22 to 29; 42 mg/kg for postnatal days 29 to 50. These concentrations in the diet were calculated to provide about 1 mg/100 gram of body weight of theobromine per day, based on total food intake. Only female pups were used for data acquisition. Male pups were either humanely euthanized by lethal injection or transferred to another protocol. In some instances, males were used to normalize suckling litter sizes.

Postnatal: Sixteen female pups per group were required for analysis, but up to 40 were utilized due to leveling of litter sizes. To minimize maternally-introduced variance during nursing, equal numbers of female neonates derived from each litter were randomized and re-allocated to each of the mothers. The appropriate diet (Thb or control) was continuously fed to the postnatal mothers. Thus, postnatal mothers fed Thb provided Thb via milk to nursing pups during the nursing interval. Pups were marked via tail tattoo or ear punch to maintain identity with offspring and dam.

Weaning: Pups were weaned 22 days after birth, when they became independent. The experimental group received theobromine in the diet continuously, until day 50, as described above.

Euthanasia: fifty days after birth, half of the pups in each group were humanely euthanized by intraperitoneal injection of pentobarbital (100 mg/kg), CO, inhalation, or inhalation overdose of isoflurane. These methods are acceptable under the guidelines of the American Veterinary Medical Association. Shortly after death was confirmed, left hindlimbs with intact femoral head were dissected from the pelvis and placed in phosphate buffered formalin for biomechanical testing. Right femurs were cut at the condyles with rongeurs, and the marrow flushed into alpha minimal essential medium ($\alpha$-MEM) containing penicillin, streptomycin and amphotericin B with 2% bovine serum. Marrow cells, preserved on wet ice in sterile media, were shipped via courier to the Institute for Regenerative Medicine for analysis.

Example 4: Human MSC (hMSC) Protocol

Theobromine (Thb): Thb was prepared as 100$\times$-1000$\times$ aliquots on water by warming at 60° C. for 15 min prior to centrifugation at 2500 g for 15 min. Because the solubility of Thb in water is frequently incomplete and unstable at the concentrations required for generation of stock solutions, spectrophotometry at 260 nm was used to confirm concentration of stocks. With warming, it was possible solubilize about 500 mg in 50 mL of water, which is close to the published solubility in the Merck index. It was noted that storage at 4° C. caused solubility to drop substantially, necessitating re-solubilization at each media replenishment.

Initially, 0, 1 and 10 $\mu$mol/mL (0.180-1.80 $\mu$g/mL) of theobromine (Thb) were used in hMSC differentiation assays in a carrier comprised of 10 mM $NH_4OH$. For the current assays, cells were tested with 1-500 $\mu$mol/mL (0.18-90 $\mu$g/mL). The volume of carrier ($NH_4OH$) necessary to attain these concentrations did not affect the pH of the culture, but substantially inhibited osteogenic differentiation. Thus, although the solubility of Thb in water is about half that of an alkaline carrier, water was used water as a carrier because the amount of water that can be added to hMSC cultures is much higher.

Water solutions of Thb are unstable until diluted to a working concentration. The extinction coefficient of Thb in $H_2O$ was calculated at 260 nm and stock solutions screened after warming to confirm the amounts added to the cells. With this protocol, a maximum of 100 µg/mL was added to media.

General MSC Protocol: For hMSCs, bone marrow cells were recovered and supplied by the Tulane adult stem cell distribution facility, New Orleans, La. in accordance with Institutional Review Board approval. Nucleated cells were recovered from the bone marrow by discontinuous density gradient centrifugation using Ficoll Paque (AP Biotech, Piscataway, N.J.). Plastic adherent, nucleated cells were separated from the aspirate by culturing in α-MEM (Gibco, Invitrogen, Carlsbad, Calif.) containing 20% (v/v) fetal calf serum (FCS; Atlanta Biochemical, Norcross, Ga.), 100 µg/mL streptomycin, 100 U/mL penicillin, and 2 mM glutamine (Gibco, Invitrogen). After 14 days in culture, adherent cells were recovered from the monolayer by incubation with 0.25% (w/v) trypsin and 1 mM EDTA (Fisher Lifesciences; Pittsburgh, Pa.) for 5 to 7 min at 37° C. and re-plated at a density of 100 cells/cm$^2$. The cells were cultured with changes of media every 2 to 3 days. At semi-confluency, $10^7$ cells were frozen at −180° C. in ten 1 mL aliquots containing α-MEM, 50% (v/v) FCS and 2% DMSO (Fisher).

Alkaline Phosphatase (ALP) and Osteoprotegerin (OPG) Assays: Osteoblastogenesis was induced on confluent monolayers in 6-24 well plates by addition of complete culture medium supplemented with 5 mM sodium glycerophosphate, 50 µg/mL L-ascorbate. Thb was added to the conditions where appropriate. Medium was changed every 48 hours. After 5-10 days, ALP activity in the monolayers was measured as follows. The cells were washed once with PBS, then with 100 mM Tris HCl (pH 9.0) containing 100 mM KCl and 1 mM $MgCl_2$ (ALP buffer). After washing, 1.5 mL of a 1:2 solution of para-nitrophenylphosphate (pNPP; Fisher) and ALP buffer was added to the wells to produce a 5 mm path length between the bottom of the well and the meniscus. ALP activity as a function of pNPP metabolism ($\Delta OD405$/min) was measured using a temperature-controlled automated plate reader (FluoStar, BMG Biotech, Chicago, Ill.). The rates were compared against standards with a known concentration of ALP and normalized against cell number. OPG ELISAs (antibody set from R and D Systems) were performed on conditioned media from these assays.

Cell Number: Cells were recovered by trypsinization, then the number of cells per well was measured by nucleic acid fluorescence incorporation assay. The cells were added to 2× CyQuant dye solution (Molecular Probes Incorporated; Eugene, Oreg.). Nucleic acid intercalation-induced fluorescence was measured using a microplate fluorescence reader (FLX800; Bio-Tek Instruments Incorporated; Winooski, Vt.) set to 480 nm excitation and 520 nm emission. The degree of fluorescence was directly proportional to cell number when compared against known standards.

Transcriptome Analysis: Total RNA from 1×10$^6$ cells was isolated using an RNA isolation kit (High Pure, Roche, Nutley, N.J.) and used to synthesize double-stranded cDNA (Superscript Choice System; Invitrogen). Biotin-labelled cRNA (GeneChip In Vitro Trancription labeling Kit; Affymetrix, Santa Clara, Calif.) was transcribed, then cleaned (RNAeasy Mini Kit; Qiagen, Valencia, Calif.), fragmented, and hybridized on HG-U133 Plus 2.0 microarray chips (Affymetrix). After washing, microarray chips were stained with streptavidin-phycoerythrin (Invitrogen), amplified with biotinylated anti-streptavidin (Vector Laboratories, Burlingame, Calif.), stained with streptavidin-phycoerythrin, then scanned (GeneChip Scanner 3000, Affymetrix) using GeneChip Operating software 1.0 (GCOS, Affymetrix). Data were analyzed using dChip software. Expression levels (as functions of arbitrary densitometric values from the array scans) were used to generate lists of upregulated genes (at least 2-fold). Lists of upregulated genes were used to interrogate the tissue expression and gene ontology databases on the DAVID website run by the National Institute of Allergy and Infectious Diseases (NI-AID), NIH (available at: david.abcc.ncifcrf.gov). For tissue expression analyses, the databases are comprised of clusters of genes that are highly expressed in given tissues (this comes from a consolidation of all of the human genome/ expression data from the US, Europe and Japan). The groups vary substantially in size (e.g., the brain group is 10 times larger than the bone group) so enrichment is scored by proportions of the lists rather than the absolute number of genes that correspond with each list. The database then assigns a p-value which represents the probability that the experimental gene list (e.g., hMSCs treated with Thb) has a given proportion of tissue specific genes due entirely to chance. Such p-values become quite small because the process involves hundreds or even thousands of transcripts.

Figure 2B:
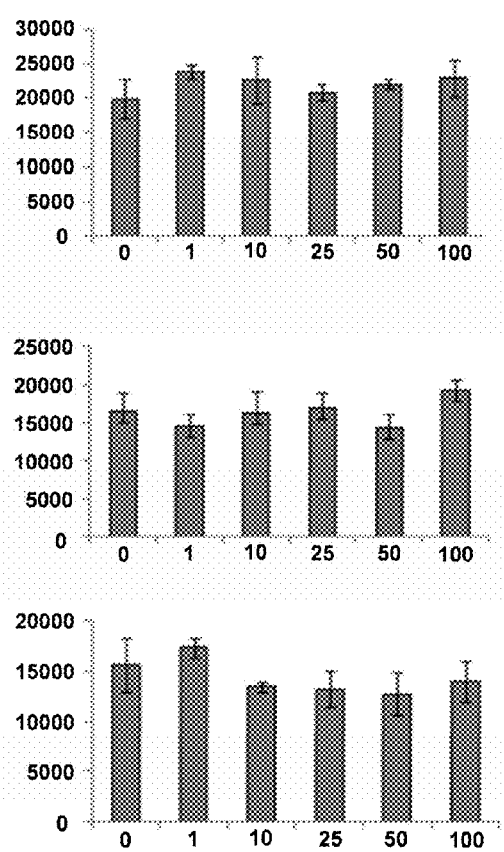

Preliminary Biochemical Assays on hMSCs: To define dosage and duration of treatment, confluent cultures of hMSCs (2 donors) were exposed to osteogenic supplements in the presence of various doses of Thb. After 5-10 days, a measurement of ALP activity or OPG secretion was carried out on the monolayers. The early osteogenic markers were upregulated by Thb in a dose dependent, biphasic manner that reached maximum effect at 100 µM Thb (FIGS. 1A & 1B). The magnitude of the increase was detectable after 4 days, but was most prominent after 8 days of exposure (data not shown). Slight cell loss was also evident at high doses, but was marginal in most cases (FIG. 1C). To further investigate the effect of Thb on osteogenic marker expression, and to finalize dosage for microarray analysis, three more hMSC donors were assayed. As previously observed, increased ALP activity was evident when cells were treated with 10-100 µM Thb for 8 days (FIG. 2).

Microarray Analyses on Thb-Treated hMSCs: Large scale cultures of hMSCs were prepared and exposed to 0, 25, 50 and 100 µM Thb for 8 days in conditions identical to those employed for the ALP and OPG assays described above. Total RNA was extracted from the cultures and subjected to microarray analysis. The following transcriptomic comparisons were made for each donor: 0 vs. 25, 0 vs. 50, 0 vs. 100 µM Thb. Those genes with more than 2-fold upregulation when compared to controls were listed. Upon examination of the data, it was apparent that although there was some inter-donor variation, the doses only cause fluctuations on fold changes rather than the identity of the genes in the list. The dose response effect confirmed that the data were robust. Given that the doses of Thb did not affect the identity of the genes in the lists, the 0 vs. 50 Thb gene lists were employed for database interrogation.

The first set of analyses were designed to address the hypothesis "Is there a statistically significant upregulation of genes commonly related to osteogenesis in hMSCs exposed to Thb?" For this purpose, the upregulated gene lists were compared to tissue expression databases using the Database for Annotation, Visualization and Integrated Discovery (DAVID) v6.7 database handler maintained by the National Institute of Allergy and Infectious Diseases (NIAID), NIH (available at david.abcc.ncifcrf.gov). For two donors tested, "bone gene" enrichment is in the top 3.5% of statistically significant tissue expression signatures (FIG. 3, donor 281; and FIG. 4, donor 7023), and this represented the first or second on the list. For donor 7057, the bone signature was in the top 9% of the list, but the overall list was longer. The variation in the size of the lists for each hMSC preparation indicates that the different cell lines exhibit different degrees of plasticity and in maximally multipotential cells, the effects of Thb seem to be pleiotropic (e.g., in 7057), whereas in hMSCs with less pluripotency bone is by far the preferred path (e.g., donors 281 and 7023). This is quite normal, since hMSCs from different donors exhibit donor-dependent variability depending on donor age, sex, degree of expansion, culture conditions etc. Nevertheless, even in profoundly pluripotent hMSC lines, bone is high on the list.

Figure 7:
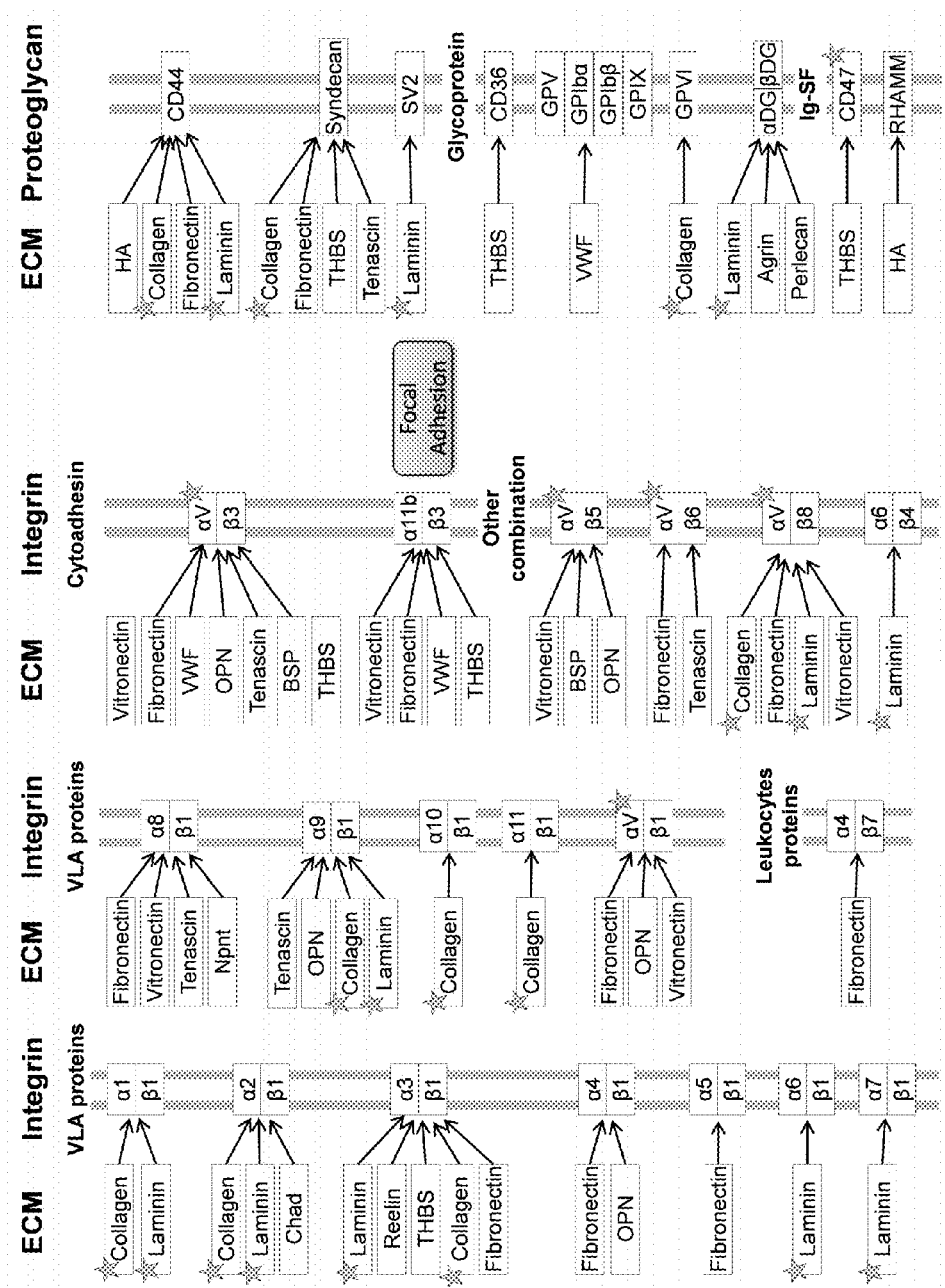
FIG. 7 shows the extracellular matrix (ECM) pathway demonstrating upregulation of collagen and alpha V integrin in Thb-treated MSCs (stars indicate genes upregulated in this data set: CD47 molecule; collagen, type XI, alpha 1; integrin, alpha V [vitronectin receptor, alpha polypeptide, antigen CD51]; and laminin, alpha 4).
Figure 8:
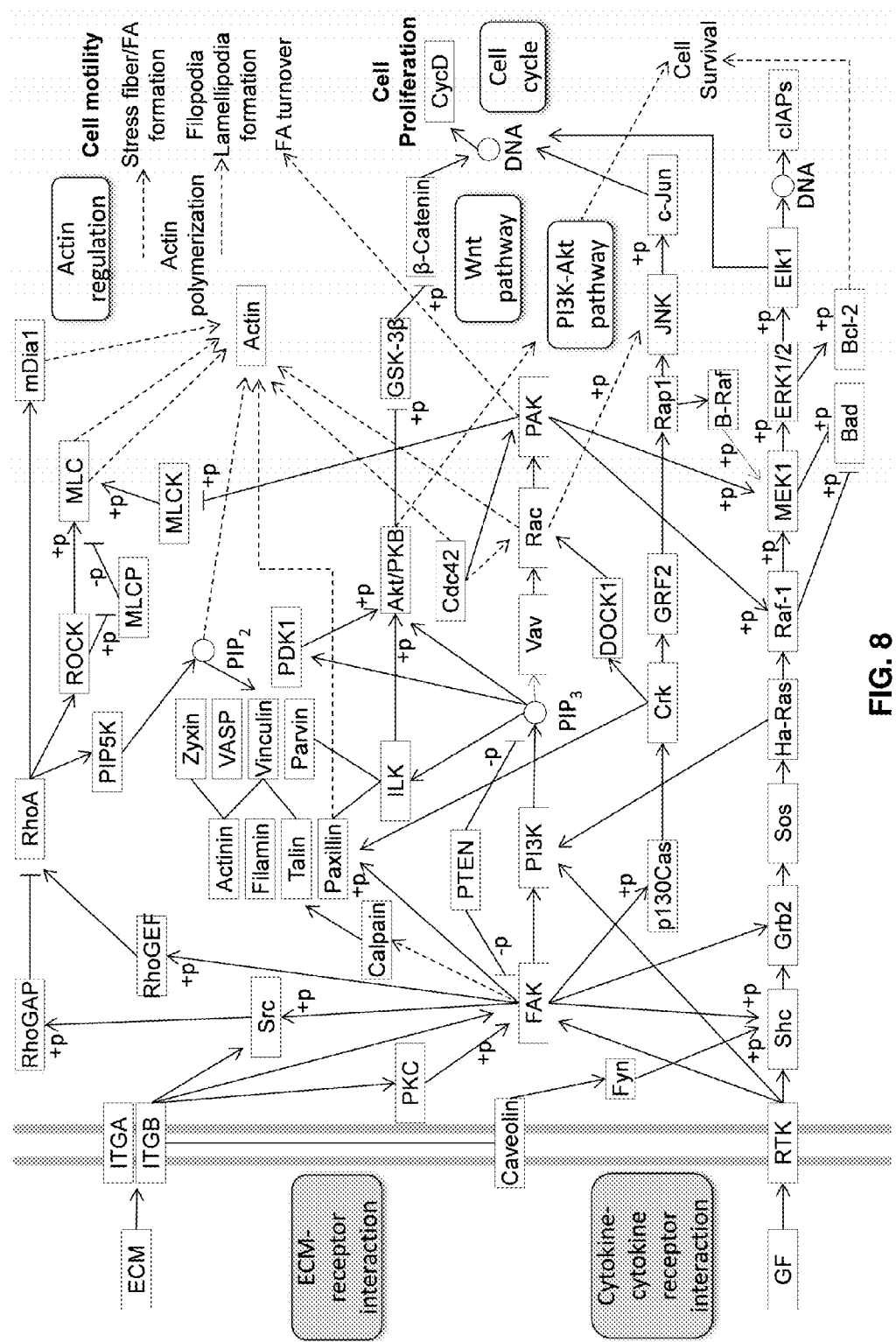
FIG. 8 shows the focal adhesion pathway demonstrating upregulation of PI3 kinase through collagen/integrin interactions (stars indicate genes upregulated in this data set: RAP1A, member of RAS oncogene family; actinin, alpha 4; collagen, type XI, alpha 1; epidermal growth factor receptor [erythroblastic leukemia viral [v-erb-b] oncogene homolog, avian]; filamin B, beta [actin binding protein 278]; glucocorticoid receptor DNA binding factor 1; glycogen synthase kinase 3 beta; integrin, alpha V [vitronectin receptor, alpha polypeptide, antigen CD51]; laminin, alpha 4; mitogen-activated protein kinase 1; phosphatase and tensin homolog, phosphatase and tensin homolog pseudogene 1; phosphoinositide-3-kinase, regulatory subunit 1 [alpha]; and son of sevenless homolog 1).

To investigate possible mechanisms of action, the lists of Thb upregulated genes were then used to probe the signal transduction pathway database to test whether Thb had a preferential molecular mode of action. There were few hits, suggesting that Thb may transduce its action through a novel pathway. Nevertheless, extracellular matrix and focal adhesion signaling pathways were significantly represented in donors 281 and 7023 (those with a highly significant osteoblast signature). ECM interations and focal adhesion signaling are generally mediated through collagen-integrin mediated pathways via PI3 kinase (see FIGS. 7 & 8). It is therefore possible that Thb causes a feed-forward loop through upregulation of collagen, integrin and PI3 kinase signaling.

Example 5: Femurs from Rats Exposed to Theobromine

The mechanical properties of femurs obtained from EXAMPLE 3 were studied at the university of Texas using protocols described by Beary (Beary D F. The effect of fluoride and low calcium on the physical properties of the rat femur. *Anat. Rec.* 1969; 164:305-316). Compared to the Beary study, however, the instant measurements were calculated automatically via computer attached to the measurement apparatus.

Briefly, an Instron Universal Testing Instrument was employed to test the femurs of EXAMPLE 3 for strength and flexibility. A special metal holding device for the femurs was used so that the diaphysis was loaded anteriorly at the midpoint The force, F, was applied midway between these supports on the anterior surface. The load at the elastic limit, maximum load, and load at the breaking point were measured on the x-axis, and the amounts of deflection at these loads were measured on the y axis. In the mechanical properties study, note that the length of the portion of each specimen that was used to make the measurement is the same, 15 mm, for all. This length is defined by the distance between the two supports at each end of the specimen, as it is placed under a load at the center, and bent until it breaks. This is called a three-point bending measurement, and produces transverse strength results. It is also known as flexure strength. UTS=ultimate transverse strength. Data from femurs of theobromine-treated rats are provided in TABLES 5.1 and 5.2, while the study parameters are provided in TABLES 5.3 and 5.4. Data from femurs of control rats are provided in TABLES 6.1 and 6.2, while the study parameters are provided in TABLES 6.3 and 6.4.

TABLE 5.1

| Specimen # | Width mm | Thickness mm | Energy To Break N*mm | Peak Load N | U Transverse Strength MPa | Modulus MPa | Strain at Break mm/mm |
|---|---|---|---|---|---|---|---|
| 1 | 3.52 | 3.01 | 40.630 | 70.87 | 63.334 | 1987.32 | 0.0458 |
| 2 | 4.20 | 2.78 | 25.079 | 71.85 | 63.083 | 3112.30 | 0.0255 |
| 3 | 4.10 | 2.70 | 32.354 | 75.68 | 72.166 | 3815.56 | 0.0279 |
| 4 | 3.75 | 2.70 | 28.230 | 56.81 | 59.230 | 3341.43 | 0.0329 |
| 5 | 3.58 | 2.72 | 25.997 | 56.30 | 60.584 | 2927.70 | 0.0321 |
| 6 | 4.10 | 2.80 | 37.889 | 72.24 | 64.048 | 3510.26 | 0.0336 |
| 7 | 3.80 | 2.80 | 26.185 | 62.43 | 59.722 | 3123.06 | 0.0295 |
| 8 | 3.79 | 2.78 | 21.103 | 54.69 | 53.210 | 2715.69 | 0.0280 |
| 9 | 3.79 | 2.78 | 22.884 | 65.09 | 63.332 | 3394.93 | 0.0258 |
| 10 | 3.79 | 2.78 | 24.809 | 67.36 | 65.543 | 3685.32 | 0.0259 |
| Mean | 3.84 | 2.78 | 28.516 | 65.33 | 62.425 | 3161.36 | 0.0307 |
| Std. Dev. | 0.22 | 0.09 | 6.441 | 7.51 | 4.889 | 531.95 | 0.0061 |

TABLE 5.2

| Specimen # | Offset Yield | Stress At Offset Yield MPa | Energy to Yield N*mm | Yield Index | Strain At Offset Yield mm/mm | Ext At Break mm |
|---|---|---|---|---|---|---|
| 1 | 340 | 30.420 | 6.529 | 340 | 0.0156 | 1.735 |
| 2 | 290 | 50.251 | 11.870 | 290 | 0.0163 | 1.162 |
| 3 | 266 | 57.176 | 12.150 | 266 | 0.0152 | 1.162 |
| 4 | 82 | 39.791 | 5.349 | 82 | 0.0122 | 0.732 |
| 5 | 197 | 35.110 | 4.971 | 197 | 0.0122 | 1.092 |
| 6 | 221 | 45.720 | 8.358 | 221 | 0.0133 | 1.168 |
| 7 | 176 | 36.320 | 5.344 | 176 | 0.0118 | 0.960 |
| 8 | 241 | 33.625 | 5.295 | 241 | 0.0126 | 1.130 |
| 9 | 201 | 43.236 | 6.945 | 201 | 0.0130 | 0.940 |
| 10 | 282 | 49.833 | 8.335 | 282 | 0.0138 | 1.193 |
| Mean | 230 | 42.148 | 7.515 | 230 | 0.0136 | 1.128 |
| Std. Dev. | 72 | 8.588 | 2.665 | 72 | 0.0016 | 0.258 |

TABLE 5.3

Calculation Inputs:

| Name | Value | Units |
|---|---|---|
| Break Marker Drop | 50.0 | % |
| Break Marker Elongation | 2.540 | mm |
| Slack Pre-Load | 4.448 | N |
| Slope Segment Length | 25.000 | % |
| Span | 19.000 | mm |
| Strain Point 1 | 0.05 | mm/mm |
| Strain Point 2 | 0.020 | mm/mm |
| Strain Point 3 | 0.020 | mm/mm |
| Yield Angle | 0.000 | rad |
| Yield Offset | 0.020 | % |
| Yield Segment Length | 2.0 | % |

TABLE 5.4

Test Inputs:

| Name | Value | Units |
|---|---|---|
| Break Sensitivity | 90 | % |
| Break Threshold | 5.000 | N |
| DataAcqRate | 10.0 | Hz |
| Extension Endpoint | 25.400 | mm |
| Initial Speed | 2.0 | mm/min |
| Load Endpoint | 4448 | N |
| Outer Loop Rate | 100 | Hz |

TABLE 5.4-continued

Test Inputs:

| Name | Value | Units |
|---|---|---|
| Slowdown Extension | 0.000 | mm |
| Slowdown Load | 0.000 | N |
| Slowdown Strain | 0.000 | mm/mm |
| Strain Endpoint | 0.100 | mm/mm |

TABLE 6.1

| Specimen # | Width mm | Thickness mm | Energy To Break N*mm | Peak Load N | U Transverse Strength MPa | Flexural Modulus MPa | Strain at Break mm/mm |
|---|---|---|---|---|---|---|---|
| 1 | 3.56 | 2.78 | 22.425 | 68.39 | 70.845 | 3853.28 | 0.0241 |
| 2 | 3.74 | 2.80 | 23.743 | 61.63 | 59.899 | 3115.08 | 0.0275 |
| 3 | 3.74 | 2.71 | 33.432 | 59.57 | 61.808 | 3132.35 | 0.0357 |
| 4 | 3.45 | 2.71 | 31.500 | 64.41 | 72.445 | 3772.38 | 0.0309 |
| 5 | 3.52 | 2.60 | 27.890 | 56.25 | 67.373 | 4259.04 | 0.0301 |
| 6 | 3.65 | 2.78 | 24.838 | 67.30 | 67.995 | 3826.32 | 0.0253 |
| 7 | 3.50 | 2.61 | 16.902 | 55.33 | 66.138 | 3363.08 | 0.0226 |
| 8 | 3.20 | 2.78 | 22.344 | 66.56 | 76.704 | 3577.97 | 0.0255 |
| 9 | 3.90 | 2.78 | 24.778 | 70.68 | 66.834 | 3442.42 | 0.0257 |
| 10 | 3.52 | 2.60 | 24.530 | 61.29 | 73.413 | 3026.66 | 0.0294 |
| Mean | 3.58 | 2.72 | 25.238 | 63.14 | 68.346 | 3536.86 | 0.0277 |
| Std. Dev. | 0.19 | 0.08 | 4.741 | 5.19 | 5.174 | 394.91 | 0.0039 |

TABLE 6.2

| Specimen # | Offset Yield | Stress At Offset Yield MPa | Energy to Yield N*mm | Yield Index | Strain At Offset Yield mm/mm | Ext At Break mm |
|---|---|---|---|---|---|---|
| 1 | 270 | 52.824 | 8.728 | 270 | 0.0139 | 1.110 |
| 2 | 248 | 42.502 | 7.403 | 248 | 0.0139 | 1.110 |
| 3 | 236 | 44.350 | 7.829 | 236 | 0.0144 | 1.250 |
| 4 | 304 | 64.991 | 13.120 | 304 | 0.0174 | 1.300 |
| 5 | 195 | 46.130 | 5.435 | 195 | 0.0111 | 1.080 |
| 6 | 300 | 53.524 | 10.001 | 300 | 0.0142 | 1.228 |
| 7 | 222 | 53.334 | 9.224 | 222 | 0.0161 | 0.880 |
| 8 | 249 | 68.004 | 13.691 | 249 | 0.0193 | 0.955 |
| 9 | 265 | 47.221 | 8.980 | 265 | 0.0139 | 1.128 |
| 10 | 158 | 52.823 | 9.761 | 158 | 0.0177 | 0.790 |
| Mean | 245 | 52.570 | 9.417 | 245 | 0.0152 | 1.083 |
| Std. Dev. | 46 | 8.387 | 2.485 | 46 | 0.0024 | 0.164 |

TABLE 6.3

Calculation Inputs:

| Name | Value | Units |
|---|---|---|
| Break Marker Drop | 50.0 | % |
| Break Marker Elongation | 2.540 | mm |
| Slack Pre-Load | 4.448 | N |
| Slope Segment Length | 25.000 | % |
| Span | 19.000 | mm |
| Strain Point 1 | 0.05 | mm/mm |
| Strain Point 2 | 0.020 | mm/mm |
| Strain Point 3 | 0.020 | mm/mm |
| Yield Angle | 0.000 | rad |
| Yield Offset | 0.020 | % |
| Yield Segment Length | 2.0 | % |

TABLE 6.4

Test Inputs:

| Name | Value | Units |
|---|---|---|
| Break Sensitivity | 90 | % |
| Break Threshold | 5.000 | N |
| DataAcqRate | 10.0 | Hz |
| Extension Endpoint | 25.400 | mm |
| Initial Speed | 2.0 | mm/min |
| Load Endpoint | 4448 | N |
| Outer Loop Rate | 100 | Hz |
| Slowdown Extension | 0.000 | mm |
| Slowdown Load | 0.000 | N |
| Slowdown Strain | 0.000 | mm/mm |
| Strain Endpoint | 0.100 | mm/mm |

As shown by the data of TABLES 5.1, 5.2, 6.1, and 6.2, sample width and thickness were significantly greater in the theobromine group compared to controls. Femur length was also significantly greater in the theobromine group, compared to controls.

U transverse strength (bending) in the theobromine group (62.4252 MPa) was significantly less than the control group (68.3454 MPa).

Modulus (stiffness/rigidity) the theobromine group (3161.36) was not significantly different from that of the control group (3536.858). This result may be due to the mean cross-section of the treated group being numerically greater than that of the control group (cross-section is shown by width and thickness measurements). Consequently, a numerically greater amount of energy was required to break the bones of the treated group compared to those of the control group: Energy to break in the treated was 28.516, whereas the control was 25.238. Strength and modulus factor were measured in the cross-sectional area, so they are normalized values.

If theobromine treatment made the bones larger in cross-section, but not inherently stronger, it would take more force to break the larger (in cross-section) treated bones than the smaller control bones (as measured by peak load). But dividing a larger peak load by a larger cross-sectional area makes the modulus and strength smaller in the treated group (but statistically no different). Peak load of treated group was 65.33, whereas the control group was 63.14.

There is a trend toward greater resistance to breaking in the treated group, as shown by more force (higher peak load) being required to break the bones in the treated group. Therefore, the data indicate that femurs from theobromine-treated rats are more resilient or robust than those of control rats.

Figure 9A:
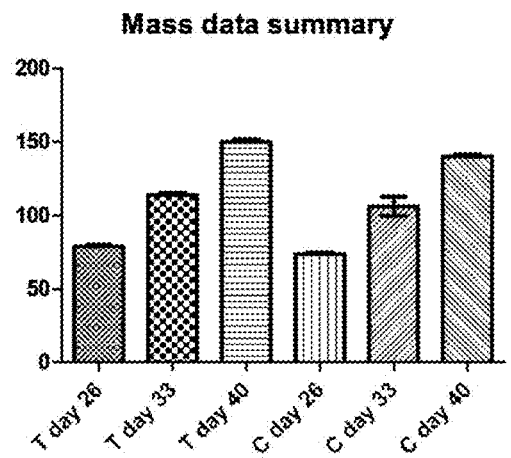
FIG. 9 (FIGS. 9A-9H) shows measurements obtained from rats of EXAMPLE 3, described below.

FIG. 9A shows the weight (grams) of rat pups in the study of EXAMPLE 3 at the days indicated. The three right-most columns indicate the weight over time of theobromine-treated rats, while the three left-most columns indicate the weight over time of the control rats.

Figure 9B:
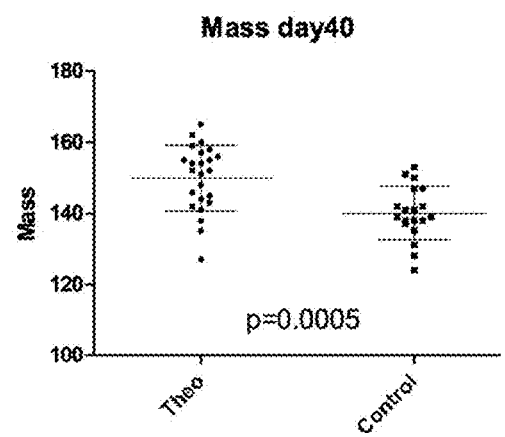

FIG. 9B shows the weight (grams) of the rat pups in the study of EXAMPLE 3 at day 40. At day 40, body weight of theobromine group was significantly greater than that of the control group. At day 47 (data not shown), the mean weight of the theobromine group was about 171 g, whereas for the control group it was about 160 g.

Bone data of FIGS. 9C, 9D, 9E, 9F, 9G, and 9H were obtained by utilizing high resolution micro-computer aided tomography to evaluate bone quality.

Figure 9C:
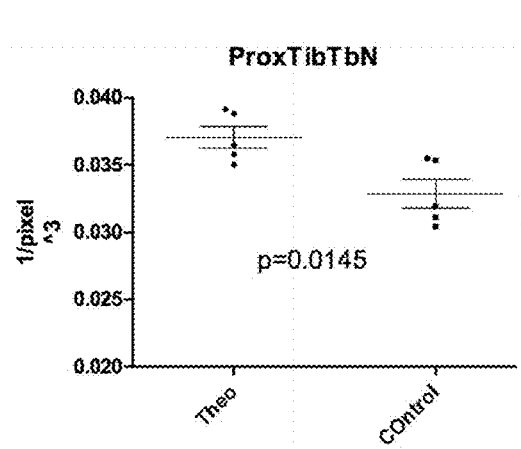

FIG. 9C shows data obtained from proximal tibia of rat pups from EXAMPLE 3, demonstrating the number of trabeculae of control and theobromine-treated rats. These data reflect the formation of bone, and demonstrate significantly more bone formation in theobromine-treated rats, versus controls.

Figure 9D:
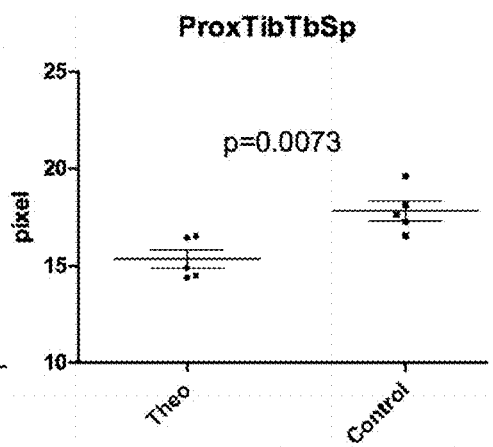

FIG. 9D shows data obtained from proximal tibia of rat pups from EXAMPLE 3, demonstrating trabecular bone spacing. Significantly less spacing between the trabecular bone was observed in the theobromine-treated group compared to the control group, suggesting greater trabecular bone formation in the theobromine-treated rats. This is a very important aspect of bone formation by feeding theobromine.

Figure 9E:
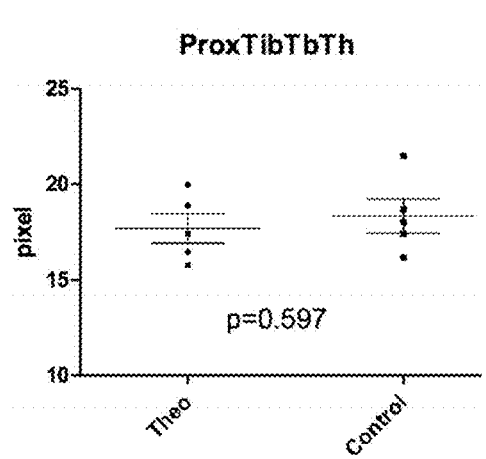

FIG. 9E shows data obtained from proximal tibia of rat pups from EXAMPLE 3, demonstrating trabecular bone thickness. No significant difference was observed between the theobromine-treated group and the control group, but these data do not indicate whether density within the hard tissue is different or not.

Figure 9F:
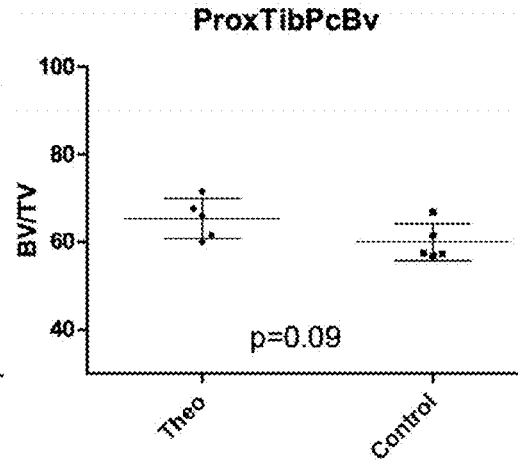

FIG. 9F shows data obtained from proximal tibia of rat pups from EXAMPLE 3, demonstrating the percent volume of trabecular bone. Although the difference between the theobromine-treated group and the control group is not statistically significant, the theobromine-treated group was slightly elevated over the control group.

Figure 9G:
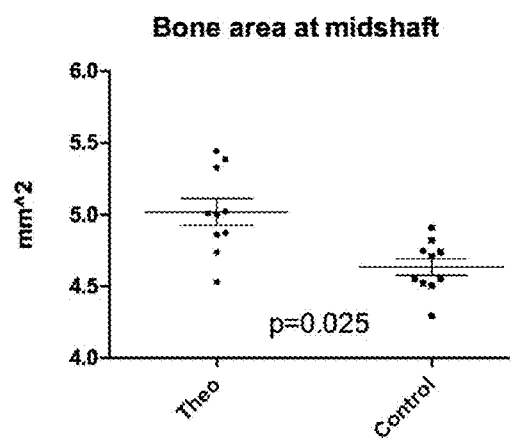

FIG. 9G shows data obtained from femurs of rat pups from EXAMPLE 3, demonstrating bone area at the midshaft of each femur. The trabecular bone area of femurs from the theobromine-treated group was significantly greater (indicating thicker bone) than that of the control group.

Figure 9H:
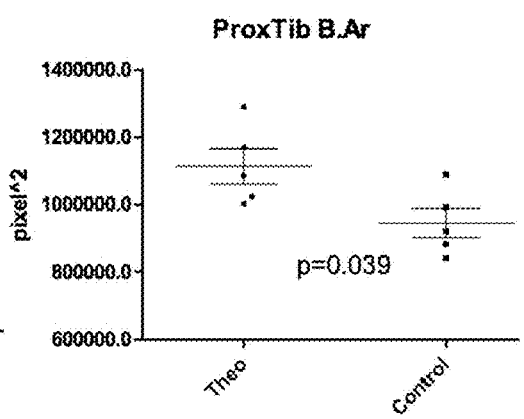
Figure 10:
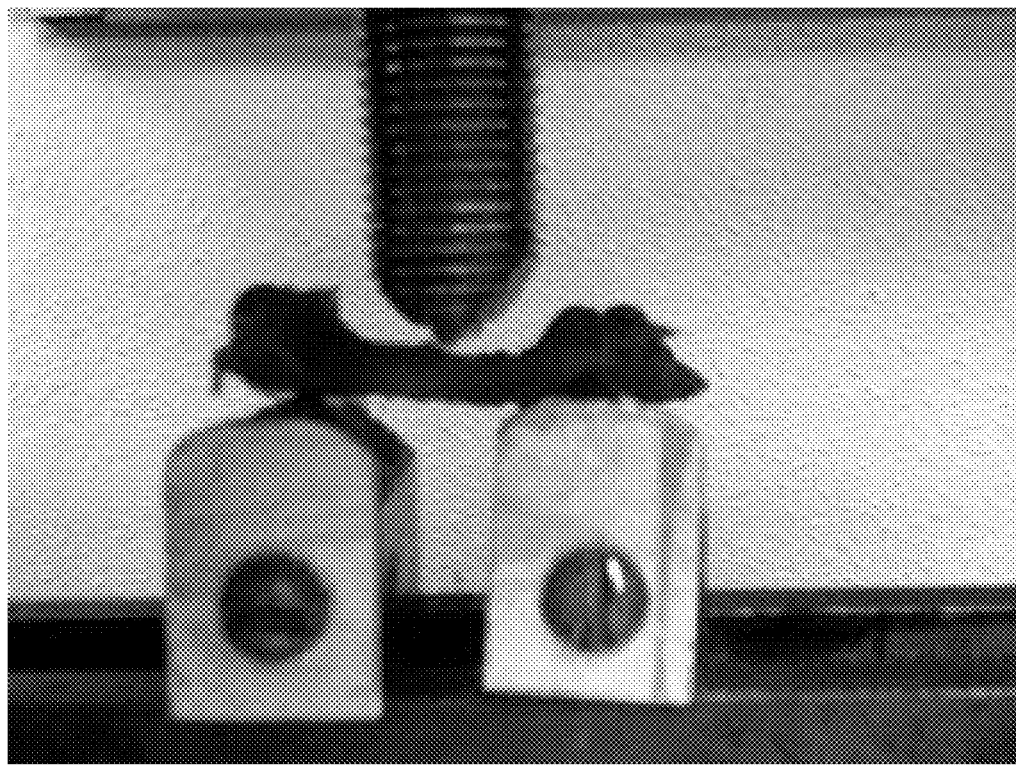
FIG. 10 shows a rat femur from EXAMPLE 3 being subjected to testing as described for, for example, FIG. 9.

FIG. 9H shows data obtained from proximal tibia of rat pups from EXAMPLE 3, demonstrating trabecular bone area. The trabecular bone area of proximal tibia of theobromine-treated rats was significantly greater (indicating thicker bone) than that of the control group.

The data of FIGS. 9A, 9B, 9C, 9D, 9E, 9F, 9G, and 9H, demonstrate that ingestion of theobromine during growth enhances body weight over time (FIGS. 9A & 9B), enhances bone formation overall (FIG. 9C), especially trabecular bone formation (FIG. 9D), and enhances bone area (FIGS. 9G & 9H).

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A method of promoting new bone growth at a bone site, consisting essentially of:
    applying to said bone site a pharmaceutical composition comprising:
    a) demineralized osteogenic bone powder with a particle size of about 0.1 mm to about 5 mm, wherein the demineralized osteogenic bone powder comprises a residual calcium content ranging between about 3% to about 10%; and
    b) theobromine, a salt or double salt of theobromine, or a co-crystal comprising theobromine, a salt, or double salt of theobromine, at a concentration of 0.027 to 270 µM.

2. The method of claim 1, wherein the demineralized osteogenic bone powder comprises a residual calcium content ranging between about 4% to about 6%.

3. The method of claim 1, wherein the demineralized osteogenic bone powder has a particle size of about 0.1 mm to about 1 mm.

4. The method of claim 1, wherein the demineralized osteogenic bone powder has a particle size of about 250 µm to about 750 µm.

5. A method of promoting new bone growth at a bone site, consisting essentially of:
    applying to said bone site a pharmaceutical composition consisting essentially of:
    a) demineralized osteogenic bone powder with a particle size of about 0.1 mm to about 5 mm, wherein the demineralized osteogenic bone powder comprises a residual calcium content ranging between about 3% to about 10%; and
    b) theobromine, a salt or double salt of theobromine, or a co-crystal comprising theobromine, a salt, or double salt of theobromine, at a concentration of 0.027 to 270 µM.

6. The method of claim 5, wherein the demineralized osteogenic bone powder comprises a residual calcium content ranging between about 4% to about 6%.

7. The method of claim 5, wherein the demineralized osteogenic bone powder has a particle size of about 0.1 mm to about 1 mm.

8. The method of claim 5, wherein the demineralized osteogenic bone powder has a particle size of about 250 µm to about 750 µm.

* * * * *